(12) United States Patent
Chou et al.

(10) Patent No.: US 7,491,852 B1
(45) Date of Patent: Feb. 17, 2009

(54) PROCESS FOR PREPARING ALDEHYDE OR KETONE BY OXIDATION OF ALCOHOL WITH A CATALYST HAVING A CORE-POROUS SHELL STRUCTURE

(75) Inventors: Kan-Sen Chou, Hsinchu (TW); Chen-Chih Chen, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 12/071,959

(22) Filed: Feb. 28, 2008

(30) Foreign Application Priority Data

Dec. 7, 2007 (TW) ............................... 96146898 A

(51) Int. Cl.
*C07C 45/29* (2006.01)

(52) U.S. Cl. ...................... 568/403; 568/471; 568/472; 568/473; 568/474

(58) Field of Classification Search ................. 568/403, 568/471, 472, 473, 474
See application file for complete search history.

(56) References Cited

OTHER PUBLICATIONS

Kan-Sen Chou et al, Fabrication and Characterization of silver core and porous silica shell nanocomposite particles; Science Direct Microporous and Mesoporous Materials 98, 2007, pp. 208-213, Elsevier Inc.

*Primary Examiner*—Sikarl A Witherspoon
(74) *Attorney, Agent, or Firm*—Bacon & Thomas, PLLC

(57) ABSTRACT

The present invention discloses a novel use of a catalyst with core-porous shell structure, which includes carrying out an oxidation of an alcohol in vapor phase and in the presence of the catalyst with core-porous shell structure to form an aldehyde or ketone, wherein the catalyst with core-porous shell structure is constituted of a core material and a porous shell material. The core material is a metal having a catalytic activity, and the shell material is a porous inorganic oxide.

16 Claims, 7 Drawing Sheets

PROCESS FOR PREPARING ALDEHYDE OR KETONE BY OXIDATION OF ALCOHOL WITH A CATALYST HAVING A CORE-POROUS SHELL STRUCTURE

TECHNICAL FIELD OF THE INVENTION

The present invention provides a novel use of a catalyst with core-porous shell structure, particularly a process for preparing aldehyde or ketone by oxidation of alcohol with a catalyst having a core-porous shell structure.

BACKGROUND OF THE INVENTION

Taiwan Patent No. 181907 discloses an improved catalyst for use in a partial oxidation of methanol to convert methanol into formaldehyde. Said catalyst includes a molybdenum oxide active catalytic material and an ingredient M, wherein M is selected from the group consisting of Cr, V, Al, W, Mn and a mixture thereof, and the molar ratio of Mo: M is of 1-5. Another improvement of this prior art invention includes using a lithic-structured inert material as a carrier of the catalyst. Said carrier is composed of $SiO_2$-rich fiber, which has an average diameter of 50 to 250 microns and a length of 2 to 30 mm. Said catalytically active material on the carrier comprises 1-90%, preferably 80-90%, of the total amount of the active material and lithic carrier.

Taiwan Patent No. 531544 discloses a process for preparing formaldehyde through a dehydrogenation reaction of methanol, which comprises performing the reaction under conditions where a carrier gas at a temperature of 300 to 1000° C. is introduced into a reactor and in the presence of a catalyst, characterized in that the temperature of the carrier gas stream entering the reactor is higher than the dehydrogenation reaction temperature for at least 20° C.

Taiwan Patent Publication No. 200624167 discloses a process for oxidizing hydrocarbons, alcohols, or aldehydes, which comprises oxidizing hydrocarbons, alcohols or aldehydes into corresponding alcohols, aldehydes, carboxylic acids or carboxylic acid esters in a liquid phase consisting of a region containing oxygen and a region substantially free of oxygen in the presence of a Pd-containing catalyst, wherein said region substantially free of oxygen comprises 0.1 to 10 vol % of the sum of said region substantially free of oxygen and said region containing oxygen.

Taiwan Patent Publication No. 200631656 discloses a process for preparing a catalyst for oxidizing methanol into formaldehyde, which comprises reacting iron powder with $MoO_2$ in an aqueous suspension solution at a Mo/Fe ratio of 1.5 to 5 and at a temperature of 20 to 100°, and subsequently, as required, using an oxidation agent to oxidize said mixture, wherein the amount of oxidation agent is equal to or greater than an amount required to oxidize ferrous ions into ferric ions and to oxidize $Mo^{+4}$ to $Mo^{+6}$ state.

Taiwan Patent Publication No. 200643004 discloses a process for preparing a concentrated formaldehyde aqueous solution, wherein methanol receives an oxidation dehydrogenation reaction at 590-690° C. in the presence of a silver catalyst to produce a 59 wt % concentrated formaldehyde aqueous solution. According to this prior art invention, the reaction medium carries away a huge amount of reaction heat, thereby promoting the oxidation reaction and achieving the objectives of high concentration of formaldehyde and low concentration of residual methanol.

Most of the conventional catalysts are prepared by depositing metal on a carrier by immersion or co-precipitation. The conventional catalysts so prepared are inevitably suffering from the defects of metal sintering under a high temperature thermal treatment environment or high temperature reaction condition, causing a great reduction in surface area of the catalyst metal, so that problems such as aging, decreasing in reaction activity or decreasing in product selectivity occur. Therefore, a new catalyst is required to replace an aged catalyst after a period of operation.

The inventors of the present application disclose a novel catalyst having a core-porous shell structure and a process for preparing the same [Microporous and Mesoporous Materials 98 (2007) 208-213 (published on the internet in October 2006)]. This novel catalyst is composed of silver nano particles and a porous $SiO_2$ shell material encapsulating the silver nano particles. Furthermore, the core-porous shell structure of this novel catalyst remains un-damaged at 1000° C. Thus, such a catalyst has the potential of being used as a catalyst for high temperature reactions. The disclosure of this article is incorporated herein by reference.

SUMMARY OF THE INVENTION

A main objective of the present invention is to provide a novel use of a catalyst with core-porous shell structure, particularly a process for preparing aldehyde or ketone by oxidation of alcohol with a catalyst having a core-porous shell structure.

Another objective of the present invention is to provide a process for preparing a catalyst with core-porous shell structure. Such a catalyst is applicable on a process for preparing aldehyde or ketone by oxidation of alcohol.

In order to accomplish the aforesaid objectives a process for preparing an aldehyde or ketone from alcohol by oxidation provided according to the present invention comprises carrying out an oxidation reaction of an alcohol in vapor phase and in the presence of a catalyst with core-porous shell structure to form an aldehyde or ketone, wherein the catalyst with core-porous shell structure comprises a core material and a porous shell material, wherein said core material is a metal having a catalytic activity, and the shell material is a porous inorganic oxide.

Preferably, said metal is selected from the group consisting of Au, Ag, Cu, Pd, Pt, Rh, Fe, Co, Ni, Mo and a mixture thereof; said shell material is selected from the group consisting of $SiO_2$, $TiO_2$, alumina, zinc oxide, tin oxide, and a mixture thereof.

Preferably, said alcohol is methanol, and said oxidation reaction forms formaldehyde.

Preferably, said metal is silver. More preferably, said core material is nano silver particles with an average particle size of 10-50 nm.

Preferably, said nano silver particles are prepared by a chemical reduction reaction using a reducing agent in an alkaline environment and using a polymer as a protective agent. More preferably, said reducing agent is formaldehyde, and said protective agent is poly(vinyl pyrrolidone) with a weight average molecular weight of about 40,000.

Preferably, said oxidation reaction is carried out in the presence of oxygen. More preferably, said oxidation reaction is carried out with a mole ratio of oxygen to methanol being 0.2-0.5.

Preferably, said oxidation reaction is carried out at 300-600° C.

Preferably, said shell material is porous $SiO_2$. More preferably, said porous $SiO_2$ has a thickness of 10-50 nm, and said porous $SiO_2$ has two major distributions in its pore sizes, wherein a relatively smaller pore size distribution thereof is about 4 nm and a relatively larger pore size distribution thereof is between 20 to 50 nm.

Preferably, the porous $SiO_2$ is prepared by a process comprising adding a polymer to tetraethyl orthosilicate used as a precursor, carrying out a hydrolysis and polycondensation of tetraethyl orthosilicate in an alkaline environment to form $SiO_2$ blended with said polymer, and removing said polymer from the blend by subjecting the blend to a thermal treatment to obtain a porous $SiO_2$. Preferably, said polymer is poly (vinyl pyrrolidone). Preferably, said thermal treatment comprises calcining the blend at 400-800° C. for 0.5-20 hours, and more preferably at 700° C. for 5-20 hours.

DETAILED DESCRIPTION OF THE INVENTION

Figure 1:
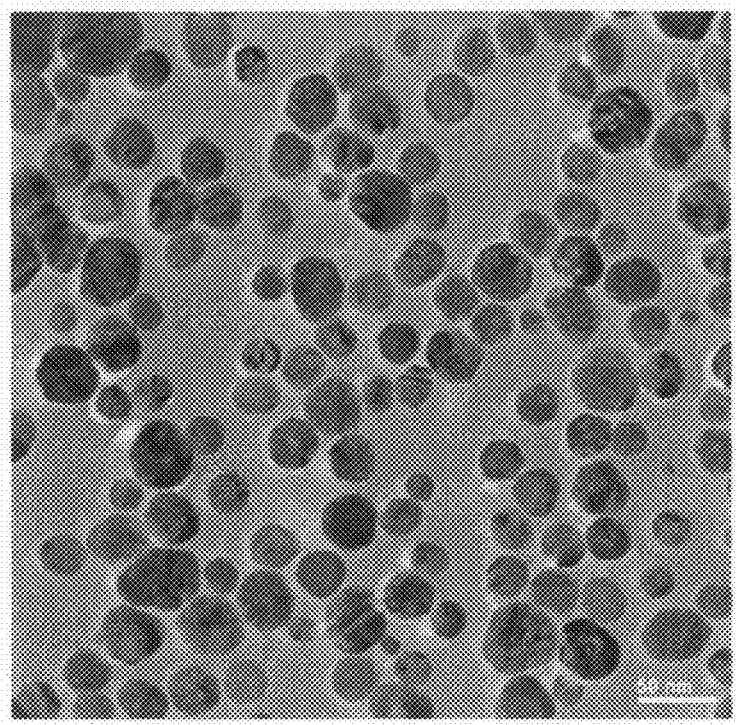
FIG. 1 is a photo taken by transmission electron microscopy (TEM) showing nano silver particles prepared in Example 1 of the present invention.

Processes for preparing an aldehyde by oxidation of a primary alcohol or secondary alcohol, processes for preparing a ketone by oxidation of tertiary alcohol are known in the prior art, for examples the patent applications described in the Background of the Invention. The gist of the present invention is to provide a substitute catalyst to improve the drawbacks of the conventional catalysts in the known processes for preparing aldehyde or ketone by dehydrogenation or oxidation reactions of an alcohol.

The substitute catalyst used in the present invention has a core-porous shell structure, wherein the core material is a metal material selected from the group consisted of Au, Ag, Cu, Pd, Pt, Rh, Fe, Co, Ni, Mo, and a mixture thereof, and can be prepared by a chemical reduction process. In one of the preferred embodiments of the present invention, Ag was used as a core material. In this embodiment, a chemical reduction process was used to reduce silver nitrate into nano silver particles under an alkaline environment, wherein formaldehyde was used as a reduction agent, and poly(vinyl pyrrolidone) (PVP) with a molecular weight of about 40,000 was used as a protective agent.

The shell material of the catalyst having a core-porous shell structure used in the present invention is an oxide such as $SiO_2$, $TiO_2$, alumina, zinc oxide, tin oxide or a mixture thereof. A suit process for preparing the shell material is a sol-gel process. For example, a shell material made of $SiO_2$ can be prepared by a sol-gel process using tetraethyl orthosilicate (TEOS) as a $SiO_2$ precursor to perform hydrolysis and polycondensation reactions of TEOS in an alkaline environment. In order to form a porous $SiO_2$ shell a polymer is additionally added to TEOS as a template, and thus the resulting $SiO_2$ is blended with the polymer. Next, the polymer is removed form the blend to obtain a porous $SiO_2$ shell structure. In one of the preferred embodiments of the present invention, TEOS was used as a $SiO_2$ precursor, and poly(vinyl pyrrolidone) (PVP) was used as the polymer to be sacrificed by subjecting the blend to a thermal treatment.

The porous shell made of an oxide in the catalyst of the present invention has a property of high temperature resistance, thereby providing protection on internal core material and avoiding the following disadvantages: greatly reducing in surface area of the catalyst metal which is caused by sintering of the catalyst metal under a high temperature thermal treatment environment or high temperature reaction condition; ageing of the catalyst metal; and decreasing in reaction activity or in product selectivity of the catalyst metal. The core-porous shell catalyst used in the present invention is applicable on heterogeneous reactions, such as dehydrogenation reactions, hydrogenation reactions, oxidation reactions, acid-catalytic reactions, and photo-catalytic reactions.

The present invention can be better understood by the following examples, which are merely for illustrative, not for limiting the scope of the present invention.

Solution A ($H_2O$: 700 ml; PVP: 68 g; HCHO: 23.7 ml), solution B (1 M $AgNO_3$, 17.5 g $AgNO_3$ added with water to 100 ml), and solution C (6.151 g NaOH added with water to 100 ml) were prepared. Solution A and solution B were mixed and agitated vigorously, and then solution C was poured in for carrying out reaction. After the reaction had been conducted for 30 minutes, a large amount of acetone was added and the mixture was held still. Upon completion of precipitation of nano silver particles, the upper clear solution was decanted, and pure water was added for re-dispersion of nano silver particles. As shown in FIG. 1, the prepared nano silver particles are well dispersed and show no formation of agglomeration. It can be seen from FIG. 1 that the particle size distribution of the nano Ag particles prepared is within 10-50 nm, and the average particle size thereof is 27 nm.

Figure 2:
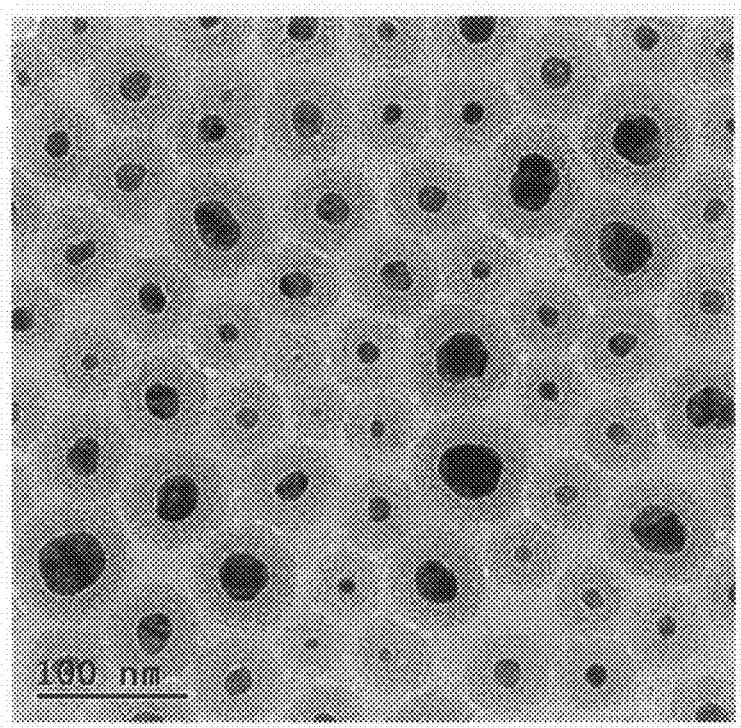
FIG. 2 is a TEM photo showing Ag-porous $SiO_2$ core-shell particles prepared in Example 1 of the present invention.

The present example used a sol-gel process to form a porous $SiO_2$ shell material. Firstly, the nano Ag particle dispersion was dispersed in a mixture solution containing ammonia water, PVP, anhydrous ethanol and deionized water, and the resulting mixture was agitated for 10 minutes to assure that they were uniformly mixed. A quantitative amount of TEOS was added into the mixture for undergoing a growing reaction of $SiO_2$ shell layer at room temperature for 24 hours. The resulting product was collected by a centrifugal means while washing with deionized water three times. The amount and concentration of the above-mentioned reactants were: Ag: 5 g/L, PVP: 10 g/L, $NH_3$: 0.3 M, $H_2O$: 13 M, $C_2H_5OH$: 13.8 M, TEOS: 0.14 M. A TEM photo of the composite particles prepared is shown in FIG. 2, which has a Ag—$SiO_2$ core-shell structure. It can be seen from FIG. 2 that a $SiO_2$ shell layer is formed on the surface of the nano Ag partilce, and the $SiO_2$ shell layer uniformly encapsulate the nano Ag particle. Furthermore, the thickness of the $SiO_2$ shell layer is not affected by the size of the nano Ag particles, which is uniformly about 30 nm regardless of the size of the nano Ag particle encapsulated therein.

Figure 3:
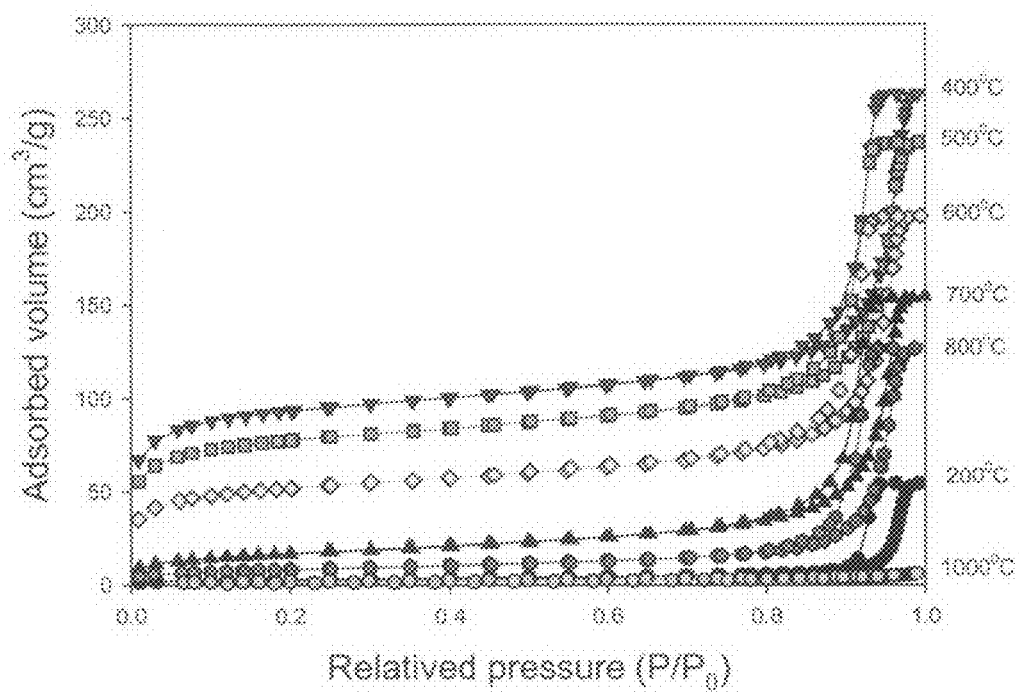
FIG. 3 shows the nitrogen adsorption/desorption curves of Ag-porous $SiO_2$ core-shell composite particles prepared by thermal treatments at different temperatures in Example 1 of the present invention.
Figure 4:
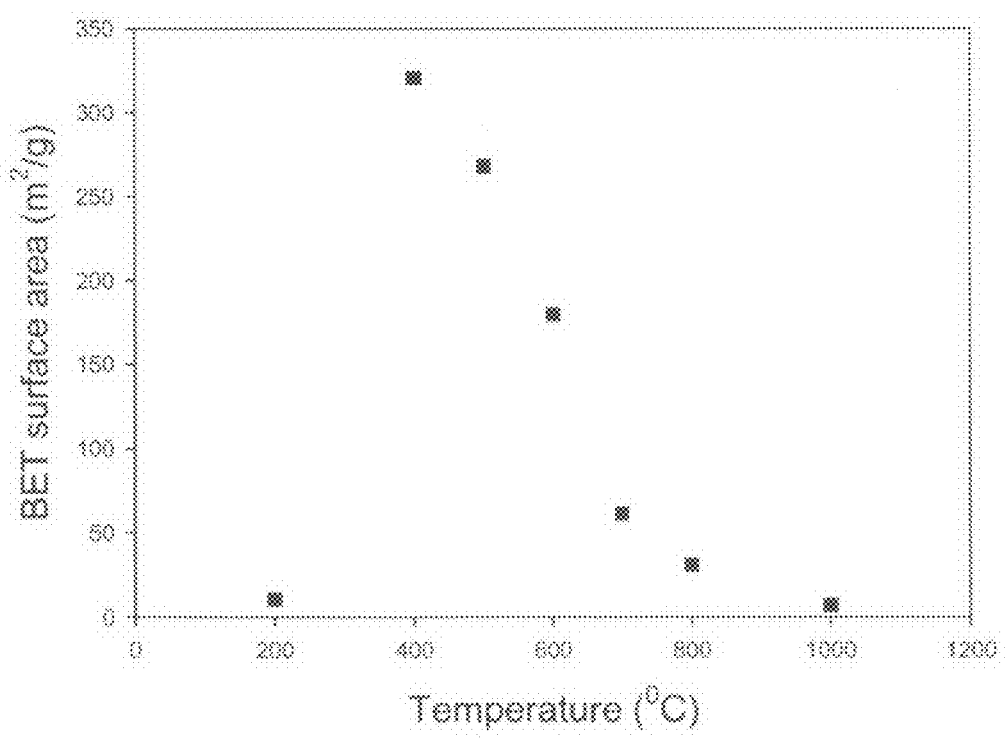
FIG. 4 shows the relationship of BET specific surface area vs. thermal treatment temperature of the Ag-porous $SiO_2$ core-shell composite particles prepared by thermal treatments at different temperatures in Example 1 of the present invention.
Figure 5:
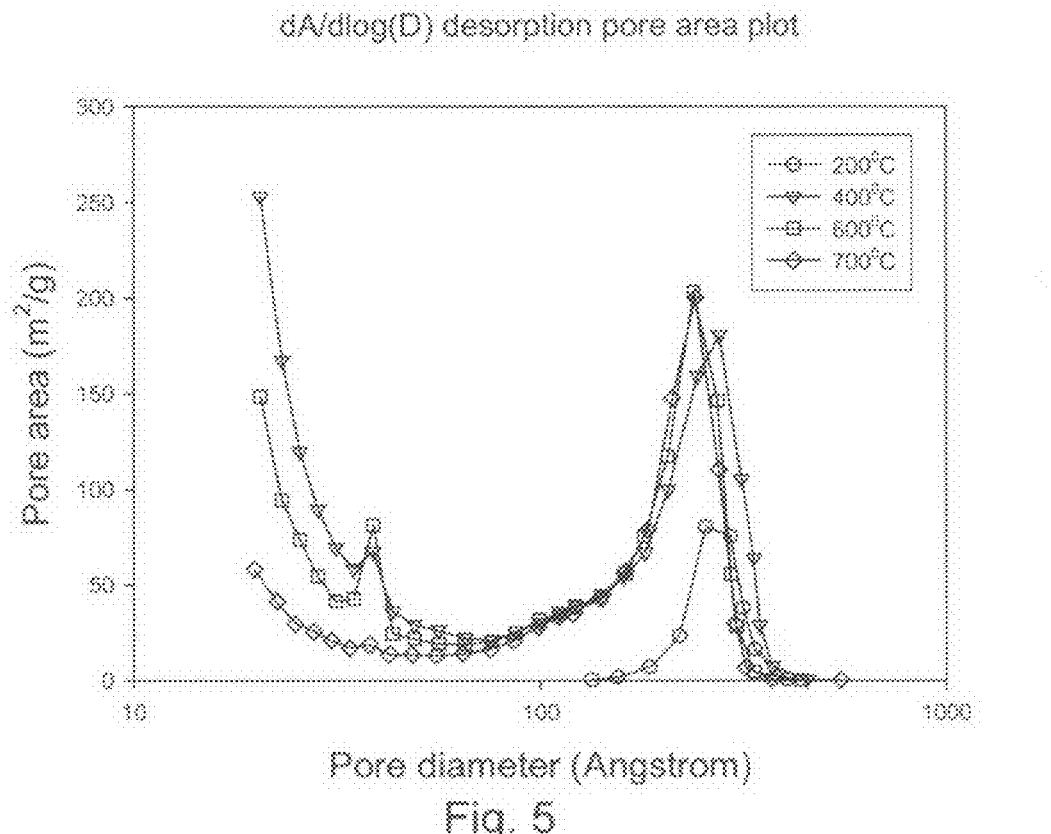
FIG. 5 is a pore size distribution plot of the Ag-porous $SiO_2$ core-shell composite particles prepared by thermal treatments at different temperatures in Example 1 of the present invention.
Figure 6:
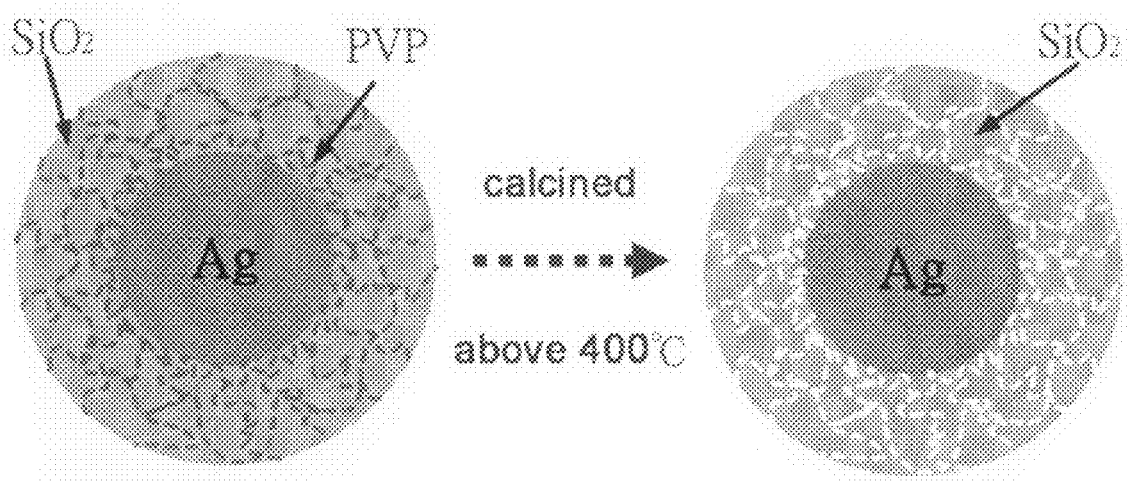
FIG. 6 is a schematic structural diagram showing the heat treatment for forming Ag-porous $SiO_2$ core-shell particles in Example 1 of the present invention.

Next, the Ag—$SiO_2$ core-shell particles was subjected to a thermal treatment to burn out the PVP embedded in the $SiO_2$ shell layer. The present example used various different thermal treatment conditions: 200° C., 0.5 hour; 400° C., 0.5 hour; 500° C., 0.5 hour; 600° C., 0.5 hour; 700° C., 0.5 hour; 800° C., 0.5 hour; and 1000° C., 0.5 hour. FIG. 3 shows nitrogen adsorption/desorption curves of the resulting Ag-porous $SiO_2$ core-shell composite particles from different thermal treatment conditions. This figure indicates that, after receiving the thermal treatments (except 1000° C., 0.5 hour), the resulting Ag-porous $SiO_2$ core-shell composite particles have a nitrogen adsorption power (i.e. a porous structure), and among them the Ag-porous $SiO_2$ core-shell composite particles subjected to the thermal treatment at 400-700° C. have a stronger nitrogen adsorption power. FIG. 4 shows the relationship between BET specific surface area of the Ag-porous $SiO_2$ core-shell composite particles and the thermal treatment temperature. As shown in FIG. 4 that, after receiving a thermal treatment at 400° C., the BET specific surface area of the Ag-porous $SiO_2$ core-shell composite particles increases drastically. The BET specific surface area decreases gradually along with an increase in the thermal treatment temperature. This is because the embedded PVP is burned our at 400° C., leaving a porous structure, so that the BET specific surface area is greatly increased. As the thermal treatment temperature exceeds 400° C., some of the pores diminish due to sintering, and this causes the BET specific surface area decreasing gradually. FIG. 5 shows the distribution of pore sizes of the Ag-porous $SiO_2$ core-shell composite particles prepared in this example. It can be seen from FIG. 5 that there are two major pore size distributions in the Ag-porous $SiO_2$ core-shell composite particles. The distribution of smaller pores is at about 4 nm or smaller, and the distribution of larger pores is within 20-50 nm. The smaller pores are developed by combustion of the PVP at high temperature, and the larger pores are formed by voids between the particles. FIG. 6 shows how the thermal treatment forms the Ag-porous $SiO_2$ core-shell composite particles.

EXAMPLE 2

Heterogeneous Catalytic Reaction of Partial Oxidation of Methanol into Formaldehyde The Ag-porous $SiO_2$ core-shell particles prepared in Example 1 were used as a catalyst in a heterogeneous reaction of partial oxidation of methanol into formaldehyde. The reaction gas composition was: $CH_3OH/O_2/H_2O$/He: 2.25/0-1/1.7/20.05-21.05. The total gas flowrate was 500 ml/min. The spatial velocity was $2.4 \times 10^4$ $hr^{-1}$, and the linear gas velocity was 6 cm/sec. The methanol conversion ratio, product selectivity and formaldehyde yield were calculated according to the following formulae:

$$\text{Conversion} = \frac{CH_3OH_{in} - CH_3OH_{out}}{CH_3OH_{in}} \times 100\%$$

$$\text{Selectivity} = \frac{\text{Product}}{CH_3OH_{in} - CH_3OH_{out}} \times 100\%$$

$$\text{Yeild} = \text{Conversion} \times \text{Selectivity}$$

Figure 7A:
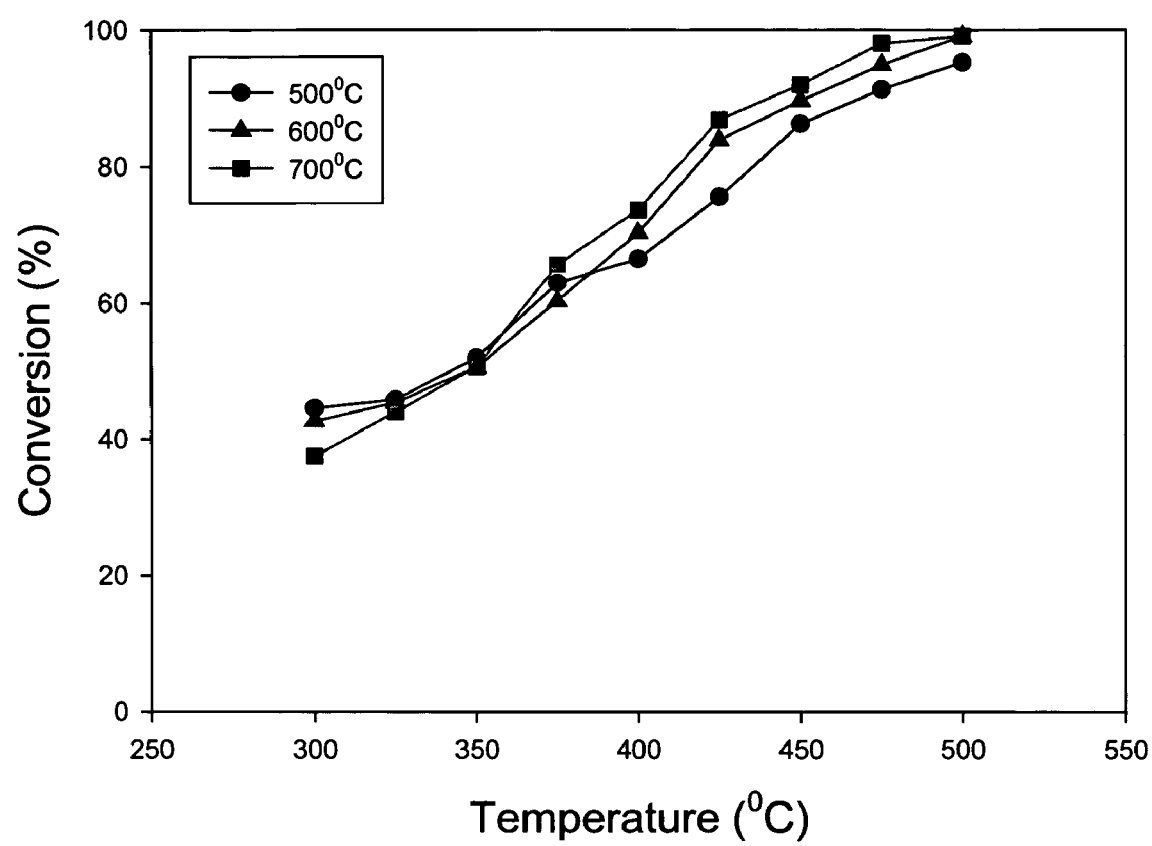
FIG. 7a shows the conversion (%) of methanol in the partial oxidation of methanol into formaldehyde by using the Ag-porous $SiO_2$ catalyst at different reaction temperatures, which were prepared by thermal treatments at different temperatures (500, 600 and 700° C. each for 5 hours).
Figure 7B:
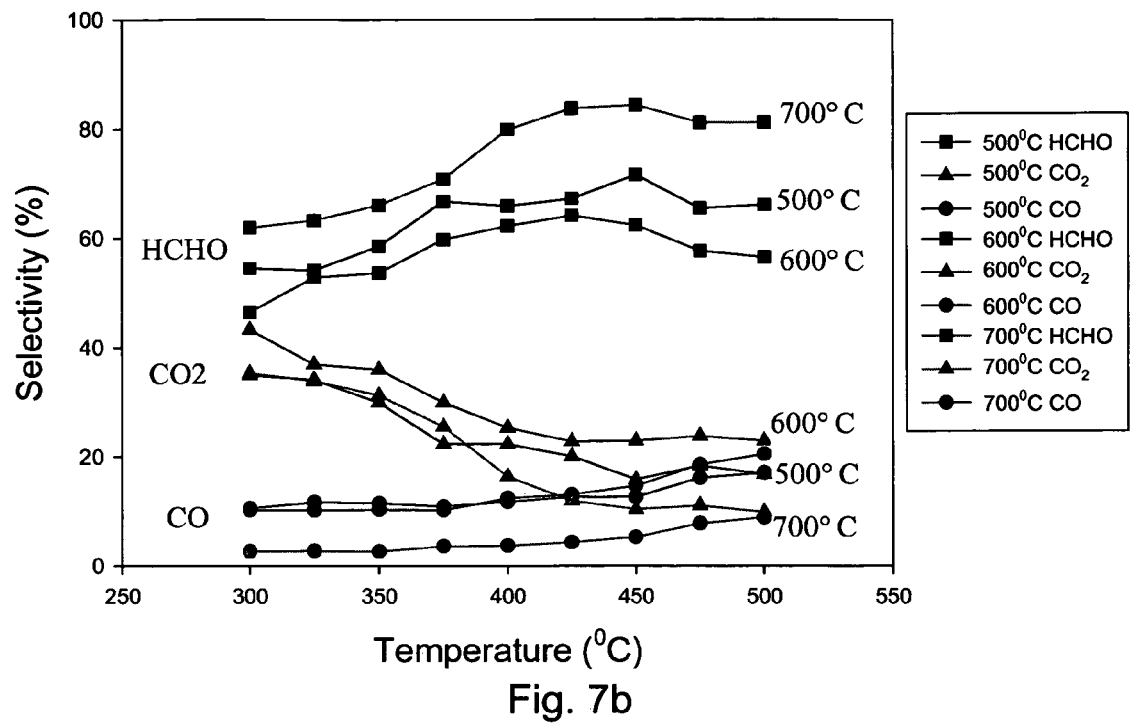
FIG. 7b shows the selectivities of products (%) in the partial oxidation of methanol into formaldehyde by using the Ag-porous $SiO_2$ catalyst at different reaction temperatures, which were prepared by thermal treatments at different temperatures (500, 600 and 700° C. each for 5 hours).
Figure 7C:
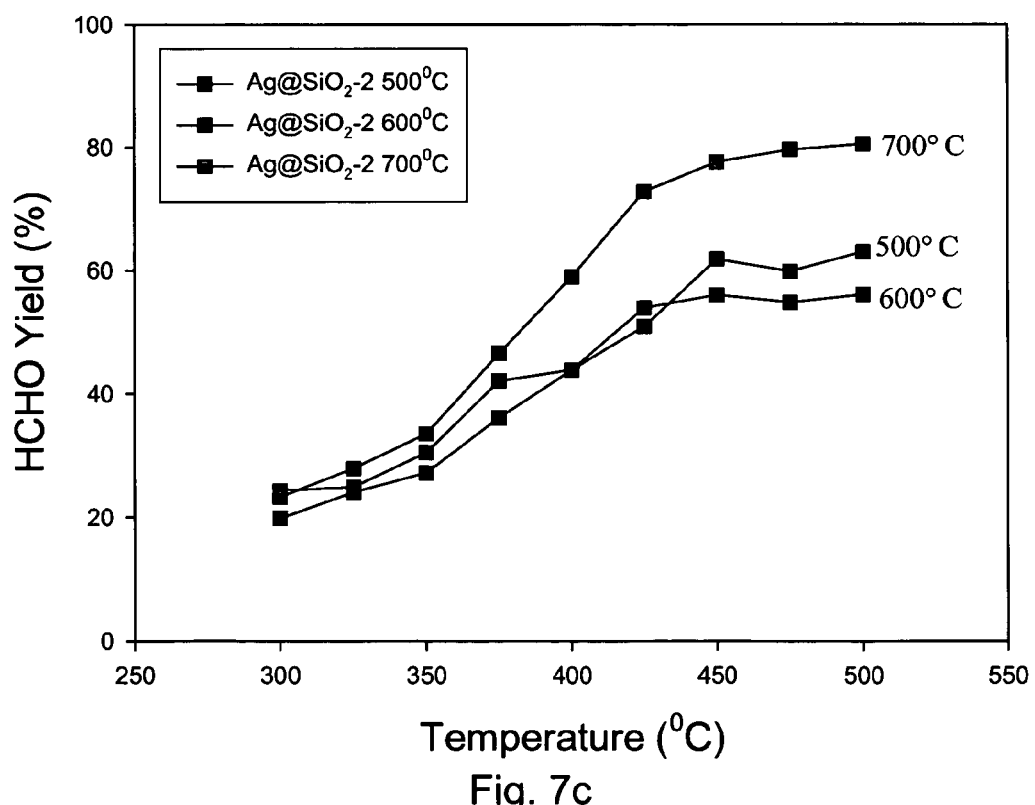
FIG. 7c shows the yield of formaldehyde (%) in the partial oxidation of methanol into formaldehyde by using the Ag-porous $SiO_2$ catalyst at different reaction temperatures, which were prepared by thermal treatments at different temperatures (500, 600 and 700° C. each for 5 hours).

The reaction results from different reaction temperatures are shown in FIGS. 7a to 7c, wherein three Ag-porous $SiO_2$ catalysts prepared at different thermal treatment conditions (500, 600 and 700° C., each for 5 hours) were used. As shown in FIG. 7a that the conversion ratio of methanol increases along with an increase in the reaction temperature. FIG. 7b indicates that the $CO_2$ selectivity decreases dramatically along with an increase in the reaction temperature; the formaldehyde selectivity increases along with an increase in the reaction temperature; and the selectivity of CO increases slightly at a higher reaction temperature (450-500° C.). FIG. 7c shows that the yield of formaldehyde increases along with an increase in the reaction temperature. Overall, the performance of the Ag-porous $SiO_2$ catalyst prepared by subjecting to a thermal treatment at 700° C. is better than those receiving the thermal treatments at 500° C. and 600° C.

Figure 8A:
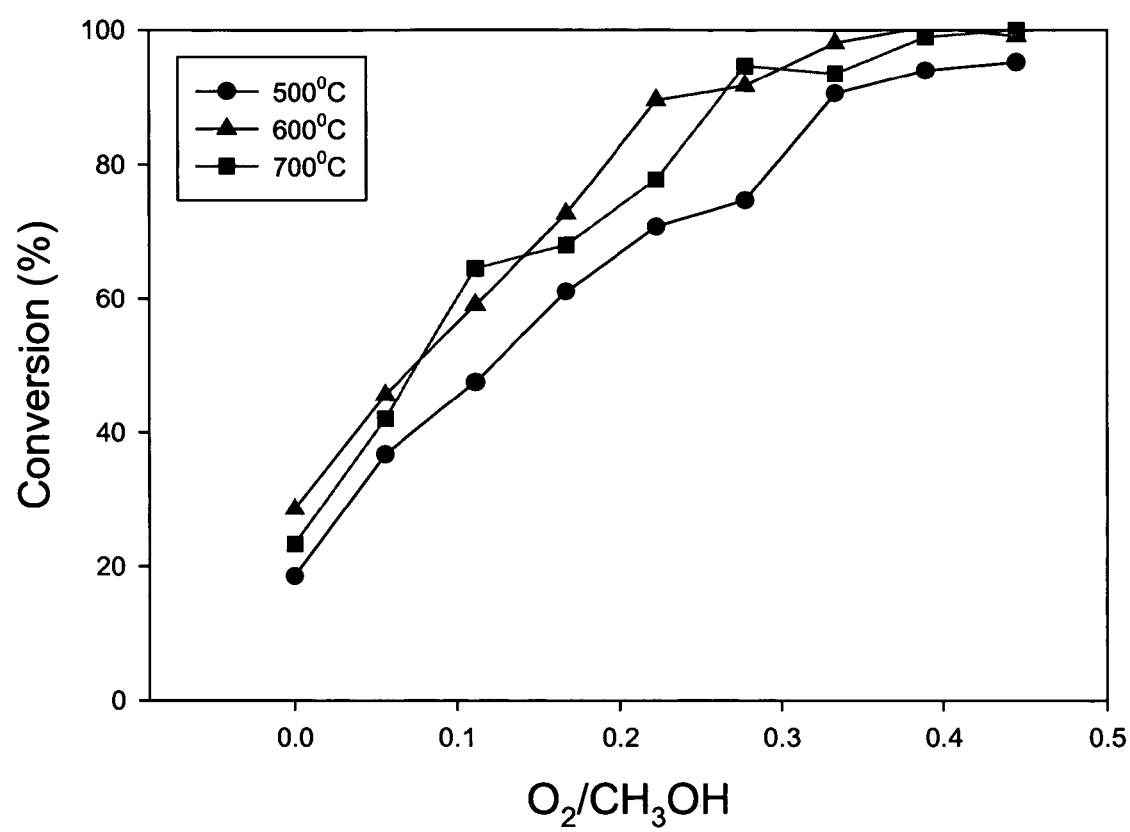
FIG. 8a shows the conversion (%) of methanol in the partial oxidation of methanol into formaldehyde by using the Ag-porous $SiO_2$ catalyst at different oxygen/methanol molar ratios, which were prepared by thermal treatments at different temperatures (500, 600 and 700° C. each for 5 hours).
Figure 8B:
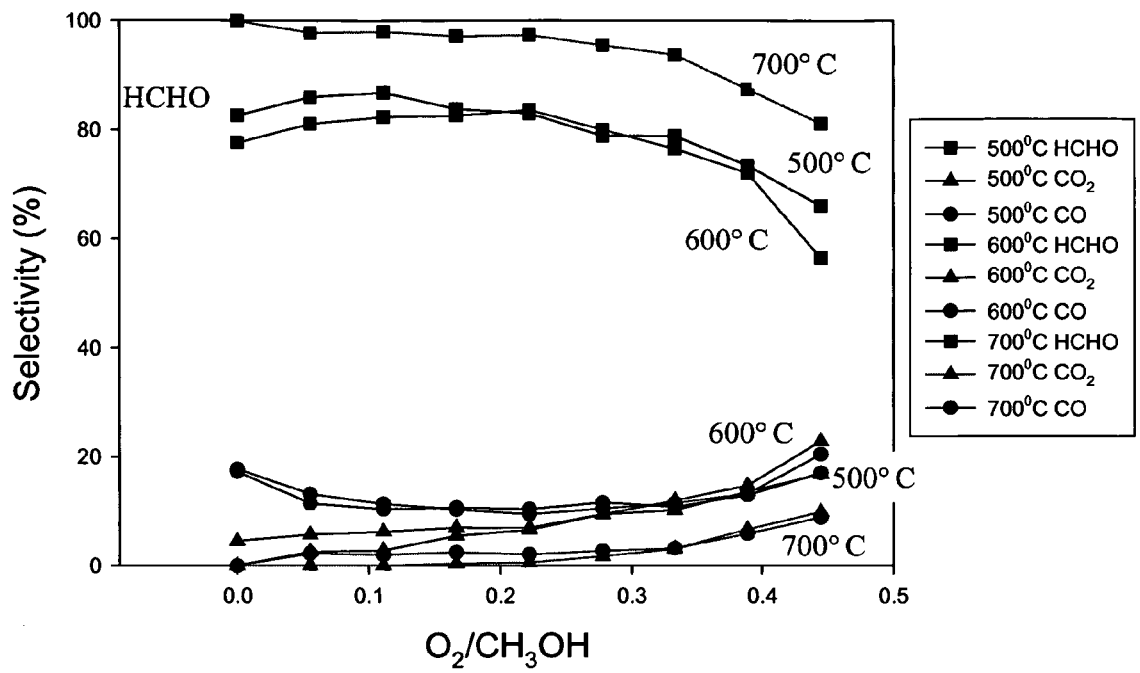
FIG. 8b shows the selectivities of products (%) in the partial oxidation of methanol into formaldehyde by using the Ag-porous $SiO_2$ catalyst at different oxygen/methanol molar ratios, which were prepared by thermal treatments at different temperatures (500, 600 and 700° C. each for 5 hours).
Figure 8C:
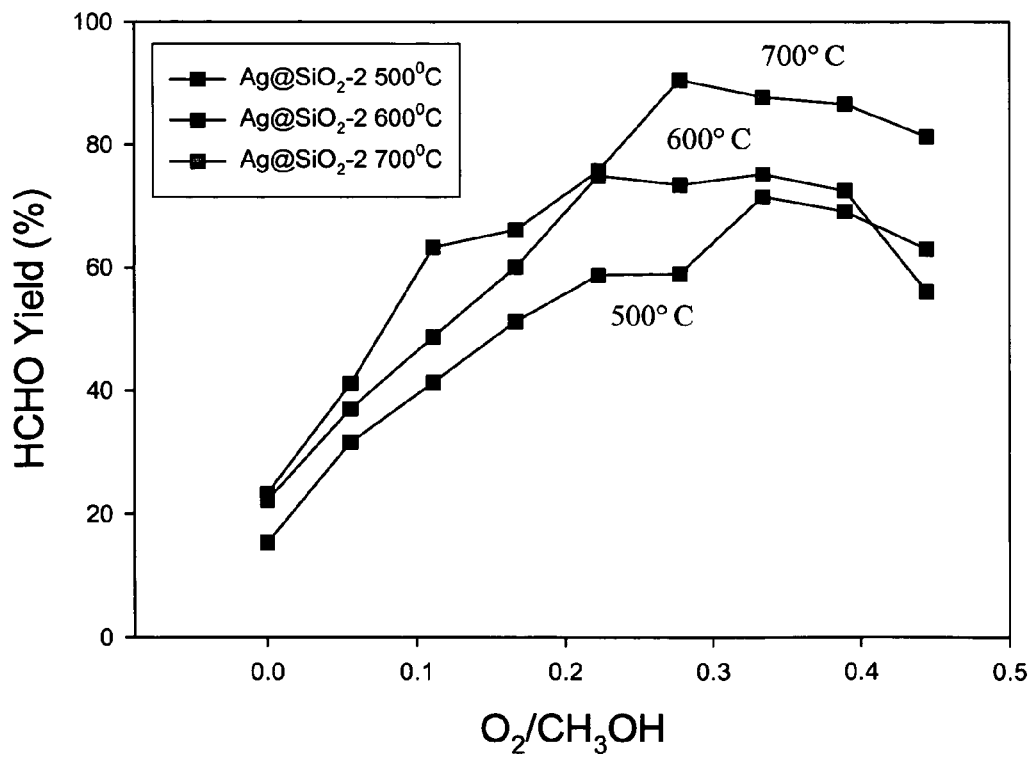
FIG. 8c shows the yield of formaldehyde (%) in the partial oxidation of methanol into formaldehyde by using the Ag-porous $SiO_2$ catalyst at different oxygen/methanol molar ratios, which were prepared by thermal treatments at different temperatures (500, 600 and 700° C. each for 5 hours).

The reaction results from different oxygen/methanol molar ratios are shown in FIGS. 8a to 8c, wherein the reaction temperature was 500° C. and three Ag-porous $SiO_2$ catalysts prepared at different thermal treatment conditions (500, 600 and 700° C., each for 5 hours) were used. As shown in FIG. 8a that the conversion ratio of methanol decreases along with an decrease in the oxygen content. FIG. 8b indicates that the formaldehyde selectivity increases along with an decrease in the oxygen concentration; and the selectivities of CO and $CO_2$ decrease as the oxygen concentration decreases. The selectivities of CO and $CO_2$ for the Ag-porous $SiO_2$ catalyst prepared by subjecting to a thermal treatment at 700° C. are lower, and the formaldehyde selectivity thereof is higher in comparison with the catalysts receiving the thermal treatments at 500° C. and 600° C. FIG. 8c shows that the yield of formaldehyde can reach upto 90% for the Ag-porous $SiO_2$ catalyst prepared by subjecting to a thermal treatment at 700° C. under the optimal oxygen concentration ($O_2/CH_3OH$: 0.28-0.39).

INDUSTRIAL APPLICATIONS

In view of the examples described above, the Ag-porous $SiO_2$ catalyst composed of a core material of Ag and a porous

The invention claimed is:

1. A process for preparing an aldehyde or ketone from an alcohol by oxidation, which comprises carrying out an oxidation reaction of an alcohol in vapor phase and in the presence of a catalyst with core-porous shell structure to form an aldehyde or ketone, wherein the catalyst with core-porous shell structure comprises a core material and a porous shell material, wherein said core material is a metal having a catalytic activity, and the shell material is a porous inorganic oxide.

2. The process as claimed in claim 1, wherein said metal is selected from the group consisting of Au, Ag, Cu, Pd, Pt, Rh, Fe, Co, Ni, Mo and a mixture thereof; said shell material is selected from the group consisting of $SiO_2$, $TiO_2$, alumina, zinc oxide, tin oxide, and a mixture thereof.

3. The process as claimed in claim 1, wherein said alcohol is methanol, and said oxidation reaction forms formaldehyde.

4. The process as claimed in claim 3, wherein said metal is silver.

5. The process as claimed in claim 3, wherein said shell material is porous $SiO_2$.

6. The process as claimed in claim 4, wherein said core material is nano silver particles with an average particle size of 10-50 nm.

7. The process as claimed in claim 5, wherein said porous $SiO_2$ has a thickness of 10-50 nm, and said porous $SiO_2$ has two major distributions in its pore sizes, wherein a relatively smaller pore size distribution thereof is about 4 nm and a relatively larger pore size distribution thereof is between 20 to 50 nm.

8. The process as claimed in claim 4, wherein said oxidation reaction is carried out in the presence of oxygen.

9. The process as claimed in claim 8, wherein said oxidation reaction is carried out with a mole ratio of oxygen to methanol being 0.2-0.5.

10. The process as claimed in claim 8, wherein said oxidation reaction is carried out at 300-600° C.

11. The process as claimed in claim 6, wherein said nano silver particles are prepared by a chemical reduction reaction using a reducing agent in an alkaline environment and using a polymer as a protective agent.

12. The process as claimed in claim 11, wherein said reducing agent is formaldehyde, and said protective agent is poly (vinyl pyrrolidone) with a weight average molecular weight of about 40,000.

13. The process as claimed in claim 5, wherein the porous $SiO_2$ is prepared by a process comprising adding a polymer to tetraethyl orthosilicate used as a precursor, carrying out a hydrolysis and polycondensation of tetraethyl orthosilicate in an alkaline environment to form $SiO_2$ blended with said polymer, and removing said polymer from the blend by subjecting the blend to a thermal treatment to obtain a porous $SiO_2$.

14. The process as claimed in claim 13, wherein said polymer is poly(vinyl pyrrolidone).

15. The process as claimed in claim 14, wherein said thermal treatment comprises cancining the blend at 400-800° C. for 0.5-20 hours.

16. The process as claimed in claim 15, wherein said thermal treatment comprises calcining the blend at 700° C. for 5-20 hours.

* * * * *